(12) United States Patent
Peaslee

(10) Patent No.: US 11,002,691 B2
(45) Date of Patent: May 11, 2021

(54) METHOD FOR DETECTING FLUORINATED CHEMICALS IN LIQUID

(71) Applicant: Graham F. Peaslee, Notre Dame, IN (US)

(72) Inventor: Graham F. Peaslee, Notre Dame, IN (US)

(*) Notice: Subject to any disclaimer, the term of this patent is extended or adjusted under 35 U.S.C. 154(b) by 335 days.

(21) Appl. No.: 15/541,267

(22) PCT Filed: Dec. 29, 2015

(86) PCT No.: PCT/US2015/067817
§ 371 (c)(1),
(2) Date: Jun. 30, 2017

(87) PCT Pub. No.: WO2016/109503
PCT Pub. Date: Jul. 7, 2016

(65) Prior Publication Data
US 2018/0266971 A1 Sep. 20, 2018

Related U.S. Application Data

(60) Provisional application No. 62/098,650, filed on Dec. 31, 2014.

(51) Int. Cl.
*G01N 23/223* (2006.01)
*G01N 33/18* (2006.01)
(Continued)

(52) U.S. Cl.
CPC ....... *G01N 23/223* (2013.01); *G01N 33/1826* (2013.01); *G01N 1/405* (2013.01);
(Continued)

(58) Field of Classification Search
CPC .......... G01N 2223/635; G01N 23/223; G01N 23/2209; G01N 23/22
See application file for complete search history.

(56) References Cited

U.S. PATENT DOCUMENTS

| 5,241,569 A | 8/1993 | Fleming |
| 6,177,008 B1 | 1/2001 | Treiber et al. |

(Continued)

OTHER PUBLICATIONS

Calzolai et al. "Proton induced γ-ray emission yields for the analysis of light elements in aerosol samples in an external beam set-up", Nuclear Instruments and Methods in Physics Research B 268 (2010), Elsevier, pp. 1540-1545 . (Year: 2010).*
(Continued)

*Primary Examiner* — David P Porta
*Assistant Examiner* — Mamadou Faye
(74) *Attorney, Agent, or Firm* — Craig A. Phillips; Dickinson Wright PLLC

(57) ABSTRACT

An ion beam analysis method to quantitatively measure the presence of fluorinated compounds in aqueous samples. The method is a quick, cost effective, nondestructive and quantitative, screen for the presence of fluorinated compounds in solution. The present invention includes a novel method of using an ion beam analysis method (such as PIGE) in air (ex vacuo) to unambiguously easily, quickly, accurately, precisely and cost effectively identify the presence of fluorinated compounds (such as PFASs) that have been extracted from aqueous solutions. The present invention may be used with a wide variety of aqueous solutions, including environmental groundwater samples, with little processing.

4 Claims, 7 Drawing Sheets

(51) Int. Cl.
  *G01N 30/88* (2006.01)
  *G01N 1/40* (2006.01)
  *G01N 30/00* (2006.01)

(52) U.S. Cl.
  CPC ............... *G01N 2030/009* (2013.01); *G01N 2030/8845* (2013.01); *G01N 2223/104* (2013.01); *G01N 2223/652* (2013.01); *Y02A 20/20* (2018.01)

(56) References Cited

U.S. PATENT DOCUMENTS

| | | | |
|---|---|---|---|
| 6,926,930 B2* | 8/2005 | Forster | C08J 7/04 427/322 |
| 2005/0095636 A1 | 5/2005 | Warner et al. | |
| 2005/0142571 A1* | 6/2005 | Parthasarathy | C12N 15/10 435/6.16 |
| 2006/0169030 A1* | 8/2006 | Stewart | G01N 1/16 73/53.01 |
| 2009/0277838 A1* | 11/2009 | Liu | B01D 15/325 210/656 |
| 2010/0242571 A1* | 9/2010 | Brennecke | B01J 20/3276 73/23.35 |
| 2011/0293847 A1 | 12/2011 | Hastings | |
| 2012/0153138 A1* | 6/2012 | McCurdy | G01N 33/48714 250/282 |
| 2012/0276576 A1* | 11/2012 | Haddad | C08F 265/04 435/29 |

OTHER PUBLICATIONS

Llorca et al. "Development and validation of a pressurized liquid extraction chromatography-tandem mass spectrometry method for perfluorinated compounds determination in fish" Department of Environmental Chemistry, IDAEA-CSIC c/ Jordi Gtorna, 18-26, 08034 Barcelona, Spain, Journal of Chomatography A, (Year: 2009).*

Hoque et al. "Determination of Fluoride in Water Residues by Proton Induced Gamma Emission Measurements", Dhaka, Bangladesh, Fluoride vol. 35 No. 3 2002 Research Report pp. 176-184. (Year: 2002).*

Li et al. "Method development for analysis of short- and long-chain perfluorinated acids in solid matrices", Taylor & Francis, Inter. J. Environ. Anal. Chem. vol. 91, No. 12, Oct. 2011, p. 1117-1134 (Year: 2011).*

International Search Report dated Feb. 23, 2016 (PCT/US2015/067817).

Robertson et al., Fluorine in Coal and Coal By-Products. Presented at: Symposium on a Trace Element Geochemitry OP Coal and Related Fuels; Spring 1994; San Diego, CA. Retrieved from the internet [retrieved Feb. 11, 2016] <https://web.anl.gov/PCS/acsfuel/preprint%20archive/39_2_SAN%DIEGO_03-94.htm>.

Hashiguchi et al., Fluorine mass balance in electrolytic degradation of perfluorooctane sulfonate in aqueous solution, May 22, 2015, International Journal of PIXE, vol. 23, Nos. 3 & 4 (2013) 153-170.

* cited by examiner

METHOD FOR DETECTING FLUORINATED CHEMICALS IN LIQUID

CROSS-REFERENCE TO RELATED APPLICATIONS

This application is a 371 national phase entry of PCT/US2015/067817, filed on Dec. 29, 2015, which claims benefit of provisional application No. 62/098,650 filed Dec. 31, 2014, the entire contents of which are incorporated herein by reference for all purposes.

BACKGROUND OF INVENTION

1. Field of Invention

The present invention generally relates to the field of ion beam analysis, where charged particles (ions) are accelerated to bombard a material to identify certain characteristics of the material, such as the elemental composition or thickness. The present invention provides a method of concentrating fluorinated compounds in aqueous solutions onto a solid substrate, and then using ion beam analysis to determine the absence, presence, or amount of fluorinated compounds in water samples.

2. Description of Prior Art

Ion beam analysis is used to study the surface characteristics of solid materials. Various types of particle accelerators are used to probe both the composition and depth of surface layers using ions of hydrogen and helium typically at megaelectonvolt ("MeV") energies. The most common example of ion beam analysis is Particle Induced X-ray Emission ("PIXE") spectroscopy, which is routinely used to measure the elemental composition of solid samples in a wide range of applications. PIXE is routinely used by geologists, archaeologists, art conservators and others to help answer questions of provenance, dating, and authenticity as it is a non-destructive technique useful in determining the elemental make-up of a material or sample. Quantum theory states that orbiting electrons of an atom must occupy discrete energy levels in order to be stable. Bombardment with ions of sufficient energy (usually MeV protons) produced by an ion accelerator, will cause inner shell ionization of atoms in a specimen. Outer shell electrons drop down to replace inner shell vacancies, however only certain transitions are allowed. X-rays of a characteristic energy of the element are emitted. An energy dispersive detector is used to record and measure these X-rays. PIXE analysis is typically performed in a vacuum, hereinafter referred to as "in vacuo", because, outside of a vacuum, the ion beam will encounter molecules in the air the beam passes through, which reduce the energy of the beam reaching the sample. This reduction in the energy of the beam may reach a point where the beam of ionized particles does not produce enough detectable x-ray emissions. PIXE is used to measure most elements heavier than silicon, and is known to be incapable of accurately measuring elements significantly lighter than silicon, such as fluorine.

A complementary application of ion beam analysis called Particle Induced Gamma-ray Emission ("PIGE") spectroscopy has been used to detect the presence of low-mass elements such as lithium, boron, sodium and fluorine, typically in geological and biological materials. PIGE analysis is also typically performed in vacuo and with solid samples for the same reasons as stated above with regard to PIXE.

Both PIXE and PIGE analysis have not been used to determine absence or presence of a target analyte in aqueous samples, and PIGE has not been used to determine whether fluorinated chemicals are present in aqueous samples. As stated above, while PIXE and other techniques are routinely used to characterize the elemental composition of materials, PIXE is not able to measure light elements such as fluorine, and as both PIXE and PIGE are performed in a vacuum, aqueous samples are not able to be used, because the liquid is boiled off as the vacuum is applied. In view of the above limitations, currently both PIXE and PIGE are currently not capable of being used to detect the presence or absence of fluorinated chemicals in samples of aqueous samples materials, such as environmental groundwater samples.

To measure the presence of perfluorinated or polyfluorinated alkyl substances (commonly known as "PFAS(s)") dissolved in water samples, the most common method is to perform a solid-phase extraction of chemicals from the water, followed by subsequent elution into an organic solution and chromatographic separation (typically liquid chromatography) and high-resolution mass spectroscopy (typically tandem mass spectrometry). Individual compounds are identified positively in this method, and can be quantified by comparison to standard compounds of known composition.

The above-described solvent extraction technique, followed by mass spectroscopy or chromatographic separation is time consuming, labor intensive, difficult to perform, and requires destruction of the sample. For example, even when being as efficient as possible and using batch processing, a skilled lab worker will run less than twenty samples per day typically. Only being able to process up to twenty samples a day, in addition to expensive and space consuming laboratory equipment, makes the known test methods for determining PFASs in aqueous solutions very expensive per test, and slow to complete. As such, currently most tests of a single sample take weeks to complete and cost in excess of $500 per sample tested. For most groundwater testing programs, such as performed by the EPA, typically dozens, if not hundreds of samples are obtained, making the testing for PFASs in water samples cost prohibitive. Furthermore, when studying groundwater pollution, not having quick turnaround of samples may require a second site visit if a plume of groundwater pollution is determined to extend outside of the tested area. A second site visit is typically an expensive undertaking, and the testing crew may have already moved on to other sites, which may delay further testing by months.

In addition to the expense, limited processing capabilities, and time delays, another problem with the solvent extraction technique followed by quantitative analysis with high-resolution mass spectrometry is that this common method has a known inherent error rate that frequently gives false positive or false negative results. False negative results are commonly obtained because the solvent extraction technique may only extract certain PFASs, while leaving other PFASs unextracted and therefore, undetected. As such, if the sample contains a PFAS that was not the targeted PFAS (but still desirable to identify), the other PFASs may remain undetected. It has furthermore been found that when processing PFASs as a batch to minimize costs and testing time, one sample having PFASs, particularly if the sample has high levels of PFASs, may cause false positive results in other samples that are free from PFASs or contain levels of PFASs under a certain level, and were run as part of the same batch.

Therefore, there is a desire for a simple, cost effective test that eliminates or reduces false positive or negatives and can test in one simple test for all PFASs in a sample, instead of only selected PFASs.

SUMMARY OF INVENTION

The present invention includes a novel method of using an ion beam analysis method (such as PIGE) in air (ex vacuo) to unambiguously easily, quickly, accurately, precisely and cost effectively identify the presence of fluorinated compounds (such as PFASs) that have been extracted from aqueous solutions. The present invention may be used with a wide variety of aqueous solutions, including environmental groundwater samples, with little processing. The present invention will allow rapid and non-destructive quantitative determination of whether PFASs are present and furthermore, a measurement of how much fluorine is present in an aqueous sample. While the present invention may accurately measure the amount of fluorine in an aqueous sample, it may also be used as a quick, efficient and cost effective method of screening samples for the presence of fluorine, and then be used in combination with traditional chemical extraction, chromatographic separation and high-resolution mass spectrometry which are used to measure the amounts of specific PFASs present in each sample, that was already determined to contain PFASs, thereby eliminating false positive and false negative results.

The present invention is generally directed to a method of detecting the presence of a target analyte in a sample of material comprising the steps of (1) obtaining a sample of material for analysis; (2) performing a solid phase extraction on the sample of material to capture an extracted analyte on a target material; (3) creating a focused beam of charged particles using a particle accelerator; (4) directing the focused beam of charged particles against the target to interact with the extracted analyte; (5) measuring the gamma rays created by the impact of the focused beam of charged particles with the extracted analyte; and (6) analyzing the measured gamma rays to determine the absence or presence of a target analyte within the extracted analyte. It should be noted the step of obtaining could be as simple as receiving a sample from a third party. The target analyte is generally expected to be PSAS(s) for which the presence of the fluorine atom is determined. The step of creating a focused beam using the particle accelerator may vary from particle accelerator to particle accelerator.

The said step of performing a solid phase extraction may further includes the steps of: (1) providing a weak anion exchange column having a cartridge; (2) placing the sample of material in the weak anion exchange column and passing the sample of material through the cartridge; (3) drying the cartridge of the weak anion exchange column; and (4) passing an adhesive through the cartridge of the weak anion exchange column to form the target. The sample is expected to be aqueous and passed through the column with the target analyte being adhered to the cartridge. The sample of material may be drawn through the cartridge using a vacuum. The cartridge is then dried, preferably air dried, such as under a vacuum at room temperature, 16-32 degrees Celsius. The adhesive is generally any adhesive capable of binding the spheres of the cartridge into a solid mass, and would not include the same element analyzed to determine the presence or absence of the target analyte. In the present invention cyanoacrylate has found to be a suitable adhesive. The adhesive may then be air dried at room temperature and the target may be removed from the column after drying.

The present invention may include a step of preparing the weak anion exchange column before the step of placing the sample of material in the weak anion exchange column. To prepare the weak anion exchange column, the following steps may be performed: (1) eluting ammonium hydroxide in methanol through the cartridge; (2) eluting methanol through the cartridge; and (3) eluting water through the cartridge. The steps may vary depending on the type of weak anion exchange.

The particle accelerator includes a beamline structure terminating in a target end station. The target material is placed in a target end station, wherein the target and target end station are at a different pressure than the beamline structure. More specifically, the beamline structure in vacuo and the target is ex vacuo, such as at the atmospheric pressure for the target and target end station. The target end station may include a target device, such as a target wheel that can be loaded with multiple targets to allow efficient measurement of many targets. The target device is moved into position and in alignment with the beamline (the beam may also be focused on the target, but within a plan of movement, it may be easier to move the target through the beam for measurement purposes. After moving a target, the measurements are taken for that target, and the target device moves again, and the steps of directing the focused beam and measuring the gamma rays are performed; and these steps are repeated until al desired targets have been measured. Typically all targets are measured before the step of analyzing occurs. In addition, the target device may have some empty holders, which allows the beam to pass through air and not strike a target, which allows the gamma ray detector to take a background reading, with the beam on, to determine the background and subtracted it from the measured readings during the analyzing steps.

The step of obtaining a sample may further include the steps of receiving a sample of material; and remixing the sample of material. In addition, a step of centrifuging the sample of material to separate the aqueous material and the solids may be performed. The aqueous phase is then decanted into a weak anion exchange column, to start the step of performing a solid state extraction.

The step of creating a focused beam of charged particles may include the steps of: (1) producing ions with an ion source; (2) accelerating the ions with an accelerator; and (3) steering and focusing said beam to exit through an exit window formed from a thin film. The exit window is generally formed of a thin film such as Kapton, but other thin films may be used. The window is configured to separate in vacuo in a beamline structure from ex vacuo for the target, with the focused beam of charged particles traveling through air before reaching the target.

The of analyzing the measured gamma rays to determine the absence or presence of a target analyte with the extracted analyte may include the steps of looking for fluorine peaks at 110 keV and 197 keV and dividing by the total charge incident on the target.

The present invention may also be directed to method of detecting the presence of perfluorinated or polyfluorinated alkyl substances (PFAS(s)) comprising the steps of: obtaining an aqueous sample of material for analysis; performing a solid phase extraction on the aqueous sample using a weak anion exchange cartridge to capture any present PFASs in the aqueous sample; forming a target from the weak anion exchange cartridge; placing the target in a target end station of a particle accelerator, wherein the target end station and target are ex vacuo and an ion source, accelerator and beamline structure of the particle accelerator are in vacuo; creating a focused beam of charged particles with the particle accelerator; directing the focused beam of charged particles to exit the beamline structure through a thin film dividing the ex vacuo target from the in vacuo beamline structure, and wherein the focused beam of charged particles impacts the target to produce gamma rays of different energies; measuring the wavelength and quantity of gamma rays created by the impact of the focused beam of charged particles against the target; and analyzing the measured gamma rays to determine if peaks in the measured gamma rays are present at 110 keV and 197 keV to determine if fluorine in PSAS(s) is present.

The step of performing a solid phase extraction may further include the steps of pulling the aqueous sample through the cartridge under vacuum and drying the cartridge under vacuum and wherein said step of forming a target from the weak anion exchange cartridge further includes the steps of passing an adhesive through the cartridge to solidify the cartridge; air drying the cartridge at 16-30 degrees Celsius; and coupling the cartridge to a target frame. The target frame defines a hole over which the cartridge is adhered. The said step of analyzing further includes the step of determining the absence or presence of PSAS(s).

DETAILED DESCRIPTION

Figure 1:
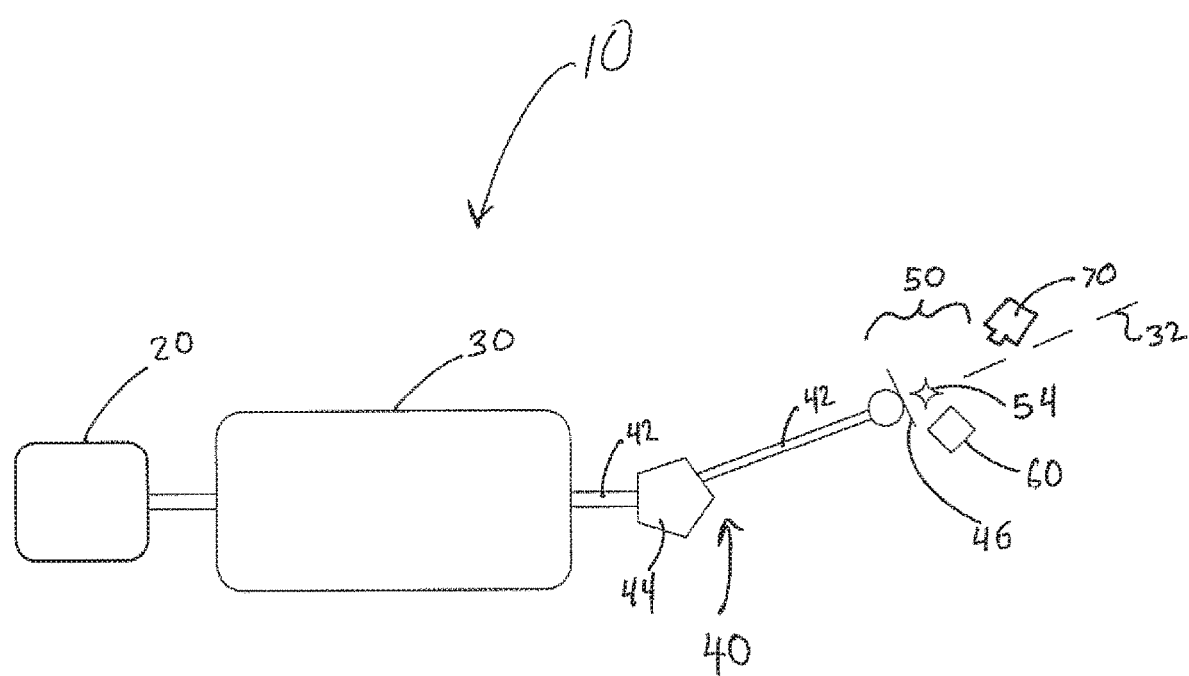
FIG. 1: A schematic representation of a particle accelerator with beam extraction into air at a target end station, and placement of target and detector.
Figure 2:
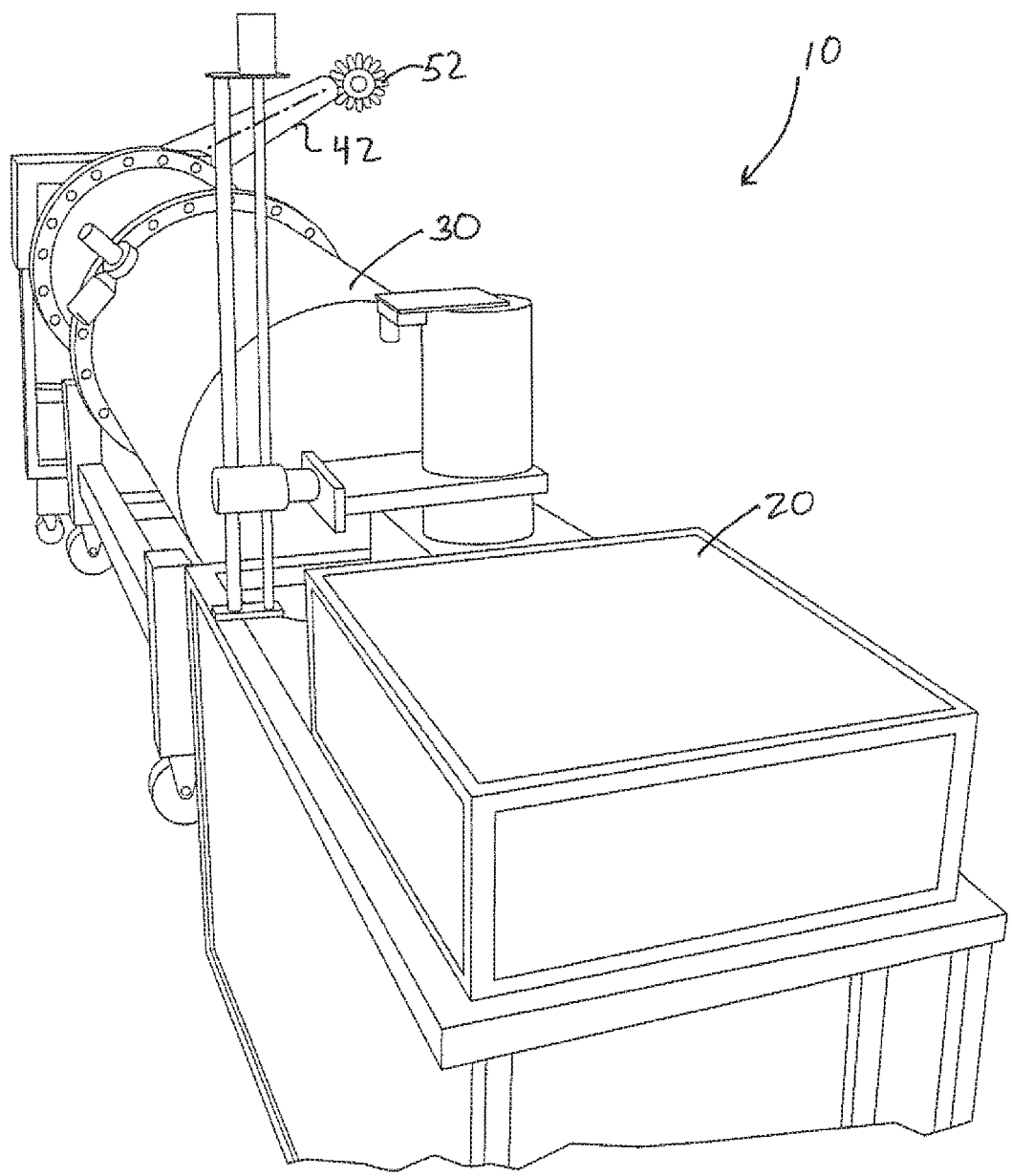
FIG. 2: A perspective view of a particle accelerator.

The present invention uses a particle accelerator 10 to detect the presence or absence of fluorinated chemicals in aqueous solutions in a cost effective, efficient and quick method. As illustrated in FIGS. 1 and 2, the particle accelerator 10 generally includes an ion source 20, which is a device to produce ionized beams of gaseous atoms, an acceleration structure 30 that propels these ions to high velocity, a beamline structure 40 including at least one beamline tube 42 that has been substantially evacuated of air. In these beamline tubes 42, the accelerated particles forming the beams can be focused and steered toward targets in at least one target end-station 50 where interactions between the accelerated ions and the sample materials occur. These interactions produce gamma ray emissions that are then measured and analyzed to determine the presence or absence of a target analyte, such as fluorine in the PFASs.

The particle accelerator 10 used for ion beam analysis in the present invention generates a beam of high-energy particles, typically ionized protons, typically with an energy between 1 and 5 MeV per nucleon. It should be noted that the application will refer to charged or ionized protons as the particles in the beam, but other charged particles could be used or substituted. In the present invention, currents of approximately 10 nA for 3.4 MeV protons were used. These proton particles are directed and focused to impact an extracted analyte from the samples of material 8 located on a target 54. The targets 54 are attached to a target frame 56 and are held in place at a target end station 50. The resultant gamma rays from the impact of the proton particles are measured with the gamma ray detector 60. Of course, liquid samples could be mounted ex vacuo for ion beam analysis, but the concentration of PFAS contaminants in groundwater are typically too low to be observed directly. Thus, a pre-concentration technique such as solid-phase extraction is typically used to concentrate the PFAS compounds onto a solid surface.

Figure 5:
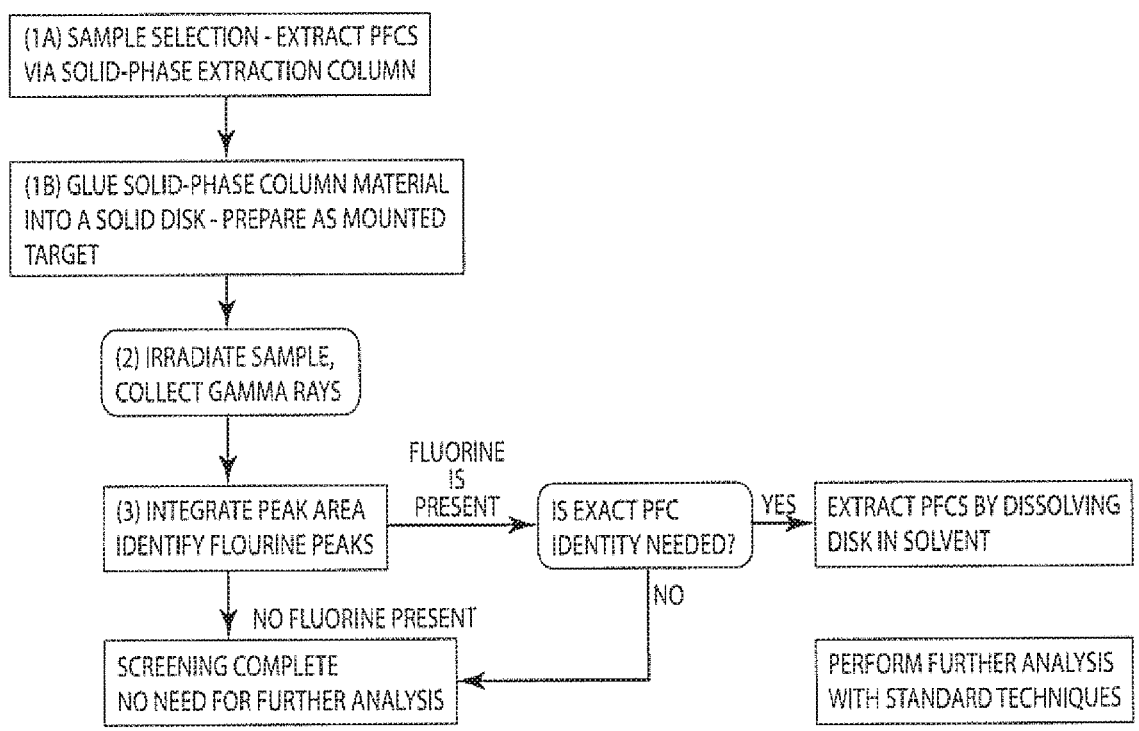
FIG. 5: A flowchart of the method.

A schematic of the typical experimental apparatus is illustrated in FIGS. 1 and 5. The solid phase extraction device 90 in FIG. 6 prepares the target 54 including an extracted analyte, for use with the particle accelerator. The particle accelerator 10 produces the ionized protons with the ion source 20, which then are directed into the acceleration structure 30, such as the illustrated electrostatic accelerator in FIG. 1. As further illustrated in FIG. 1, the particles, specifically ionized protons, are then accelerated by the accelerator structure 30 and directed into the beamline structure 40. In the present invention, the ion source 20 provides the ionized protons to the acceleration structure 30 which accelerates the ionized protons to an energy of 3.4 MeV. The accelerated ionized protons then are directed down the beamline structure 40, typically through tubes 42 in vacuo. As further illustrated in FIG. 1, magnets 44 may direct, align, focus or bend the beam of the ionized protons as desired. More specifically, the magnets cause the ionized protons to be focused as well as bend in desired directions to hit the sample of material at the target end station 50. It should be noted that any known or further developed method of creating charged particles and directing them through a beamline structure 40 toward a target 54 may be used in the present invention. However, the present invention has created in unique way of preparing and analyzing samples that are not in vacuo as in normal particle accelerators, and a unique method of analyzing groundwater samples, particularly for the presence or absence of PFASs.

The particle accelerator 10 illustrated in FIG. 1 is an electrostatic nuclear accelerator. Of course, an oscillating field accelerator may be substituted in its place and still perform the present invention. Examples of electrostatic accelerators include Cockcroft-Walton accelerators and Van De Graff accelerators, as well as a number of other types of accelerators. As long as an accelerator is capable of providing a beam of charged particles, such as ionized protons directing it toward a target 54 and has the capability of measuring the gamma ray emitted associated with PFASs, it can be used in the present invention. The accelerator 10 of the present invention also allows a novel method of not requiring in vacuo, for the targets 54. More specifically, to allow for high output and ease of measuring the samples and/or targets, the present invention allows for a novel method of not subjecting the samples to a high vacuum as previously required. The unique terminus of the beamline structure 40 and the target end station 50 of the present invention allows for the sample materials 8 and/or targets 54 to be analyzed. In addition, the present invention also uses a unique method of preparation, operation and measurement for the present invention. It should be noted that the present invention is capable of using less expensive and lower energy particle accelerators than most oscillating field accelerators as an electrostatic accelerator performs exceptionally well for the present invention.

As stated above, the present invention uses the less common particle induced gamma-ray emission (PIGE) instead of the more common particle induced X-ray emission (PIXE). When a charged particle (typically protons) approaches the nucleus of a target atom, the coulomb force usually repels it. However, when the incident particle has enough energy to overcome such coulomb force, the charged particle then passes through the electrostatic barrier into the nucleus, resulting in interactions with the nuclear forces of the target atom. The above described process results in a number of interactions with the target atom. Depending on the energy of the particle, and the type of nucleus of the target atom, typically a nuclear reaction will occur, resulting in the emission of high energy electromagnetic radiation and other nuclear particles. For historical reasons, high energy electromagnetic radiation emitted from the nucleus are called gamma rays, which the present invention measures. The PIGE process measures the emitted gamma rays, as the energies of the gamma rays emitted are correlated to the element having the target nucleus that experienced the nuclear reaction. By measuring the energies of the resulting gamma rays, the element with which a charged particle interacted may be determined. In addition, by measuring the quantity of resulting gamma rays at a certain energy, the PIGE process may not only identify what elements are present, but also quantify the concentrations of elements. The PIGE process is typically used to detect lithium (Li), fluorine (F), sodium (Na), magnesium (Mg), and aluminum (Al). The detection limits may vary, but PIGE usually can detect at least 10 ppm or less for fluorine.

As further illustrated in FIG. 1, an exemplary magnet 44 is located at a bend in the beamline structure 40. More specifically, the magnet 44 sits at the bend to change the direction of the ionized protons which normally travel in a straight line. The ionized protons exit the accelerator structure 30 and travel in a linear line down the beamline structure 40, particularly, the tubes 42. Due to space considerations, layout considerations as well as numerous other factors, magnets 44 may be included in the beamline structure 40 to direct the beam of ionized protons in a non-linear fashion. In addition, magnets 44 may also be included in other areas to tune and focus the beamline of ionized protons. Magnets 44 may also be used to track the beam across the sample in some instances. Furthermore, while FIG. 1 simplistically illustrates a magnet 44 at a sharp bend, the bend may also occur through the use of a number of magnets creating a gradual curve to the beamline of ionized protons. More specifically, a magnetic field perpendicular to the plane of motion of an accelerated particle will result in the particle taking a curved path, changing the direction of travel of the particle. By using electromagnetics or even standard magnets, the accelerated particle may be directed as desired. However, the increase in the radius of path taken by a particle is compensated for by the increased velocity of the particle if the magnetic field, the charge of the particle and the particles mass remain constant.

The target end station 50 includes a camera 70 helpful in tuning the beam for optimal performance. As stated above, the magnets 44 of the beamline structure 40 may be used to focus as well as direct the beam of charged particles. Having the beamline well focused on the sample material 8 or target 54 maximizes the ability to obtain readings of what is in the sample material 8. While a camera is not necessary to tune the beam of charged particles or beamline passing through the beamline structure 40, it is helpful to efficiently tune the beamline for optimal performance in as little of time as possible. More specifically, the specialized camera 70, such as a Sony Home Security HQ1 CCD camera, as illustrated in the figures is capable of seeing the incident ion beam when a sheet of glass is used as a target, and the ionizing radiation produces visible scintillation clearly at the end of the beamline structure 40. The window 48 is described in more detail below, but is configured to separate the in vacuo of the beamline tubes 42 from the target end station 50 which is not under a high vacuum. The camera is typically positioned to see the ion beam as it encounters the scintillating glass mounted at the target 50. It should be noted, the present invention could be used with a target end station 50 under vacuum, open to the beamline tubes 42 without the window 48, however it takes extra time to evacuate a target end station every time new targets need to be loaded, and therefore, the present invention that allows for targets to be in the open exposed to the surrounding atmosphere allows substantially higher throughput of the sample material to be analyzed.

Figure 3:
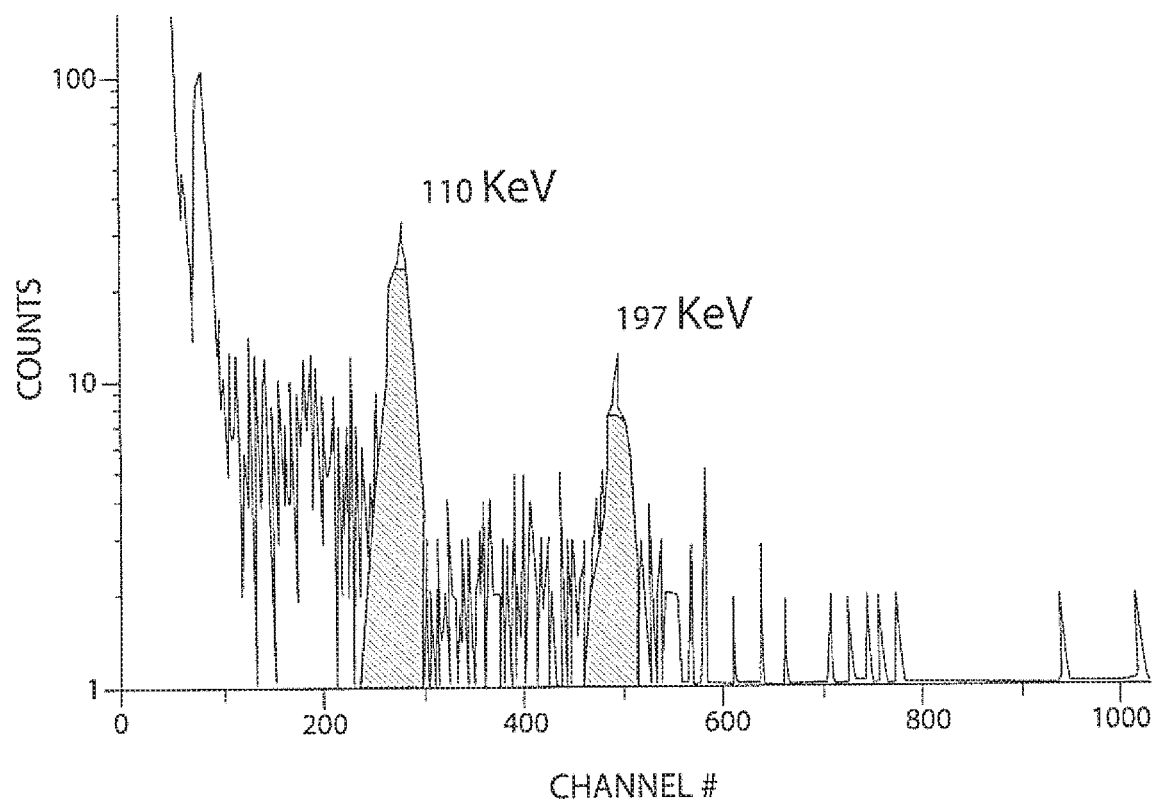
FIG. 3: An exemplary gamma-ray spectrum, including shaded regions of interest for integration of fluorine-19 peaks at 110 keV and 197 keV.

Any particle accelerator can be used to generate this ion beam, but the results displayed in FIG. 3 are from a National Electrostatics Corporation 5-SDH pelletron accelerator 30 and Alphatross® ion source configuration 20, shown in FIG. 2. This ion beam is directed through evacuated beamline structure 40, including tubes 42 using magnets 44, which may include magnetic lenses for focusing the beamline and steering elements for directing the beamline towards the window 48 and target 54. Typically, the evacuated beamline structure 40, having tubes 42, are several meters long and maintained at high vacuum levels of $10^{-7}$ torr or better. Any configuration of particle accelerator 10, including beamline structure 40, including tubes 42 and magnetic elements 44 at a vacuum that will allow delivery of a beam of accelerated particles, such as ionized protons on a target area 55 with a diameter of a few millimeters on the sample of material 8 or target 54 will work for this method. It should be noted that while the term "tube" is used to describe the elongated beamlines, any structure that allows delivery of the beam of ionized protons from one end to the other under vacuum may be used, so long as the beam may be tuned properly to hit the desired target area 55.

The beam 32 of charged particles or ionized protons 34 passes through the beamline structure 40 to arrive at the target end station 50. The target end station 50 may be made in a variety of size, shapes and configurations. Unlike the prior PIGE devices and methods, the present invention is capable of using a target end station 50 that is not under a high vacuum, although the beamline structure 50 is still under a high vacuum to maximize the number of charged particles reaching the target area 55, as well as the energy of such charged particles when they reach the target area 55. Although preferably the present invention uses a target end station 50 that is open to the surrounding atmosphere, in certain instances, it may be desirable to control the composition of surrounding air, if the ambient atmosphere contains some of the elements being analyzed. As such, the target end station 50 can be isolated from the ambient atmosphere by being enclosed and in some instances could be under a vacuum.

The target end station 50 includes a few additional unique features that allow for improved efficiency. The target station 50 includes a target wheel 52 configured to hold the targets 54, which include the extracted PFAS analytes from the aqueous samples of material 8. The whole target wheel 52, including multiple targets 54 exposed to the surrounding atmosphere, which is opposite the teaching of the prior art that has long been considered undesirable in the field of particle accelerators. A beamline passing through a vacuum may obtain and maintain a much higher energy level and as soon as the beam line with ionized protons is exposed to atmospheric conditions, it quickly loses energy. The target end station 50 may include the camera 70, gamma-ray detector 60, and target wheel 52, all of which allow for quick and efficient processing of multiple targets 54, which means multiple samples of material 8 may be quickly processed. Of course, other devices capable of moving different samples in front of the beam, may be used in place of the target wheel, and different sizes, shapes and configurations may be used.

Figure 4:
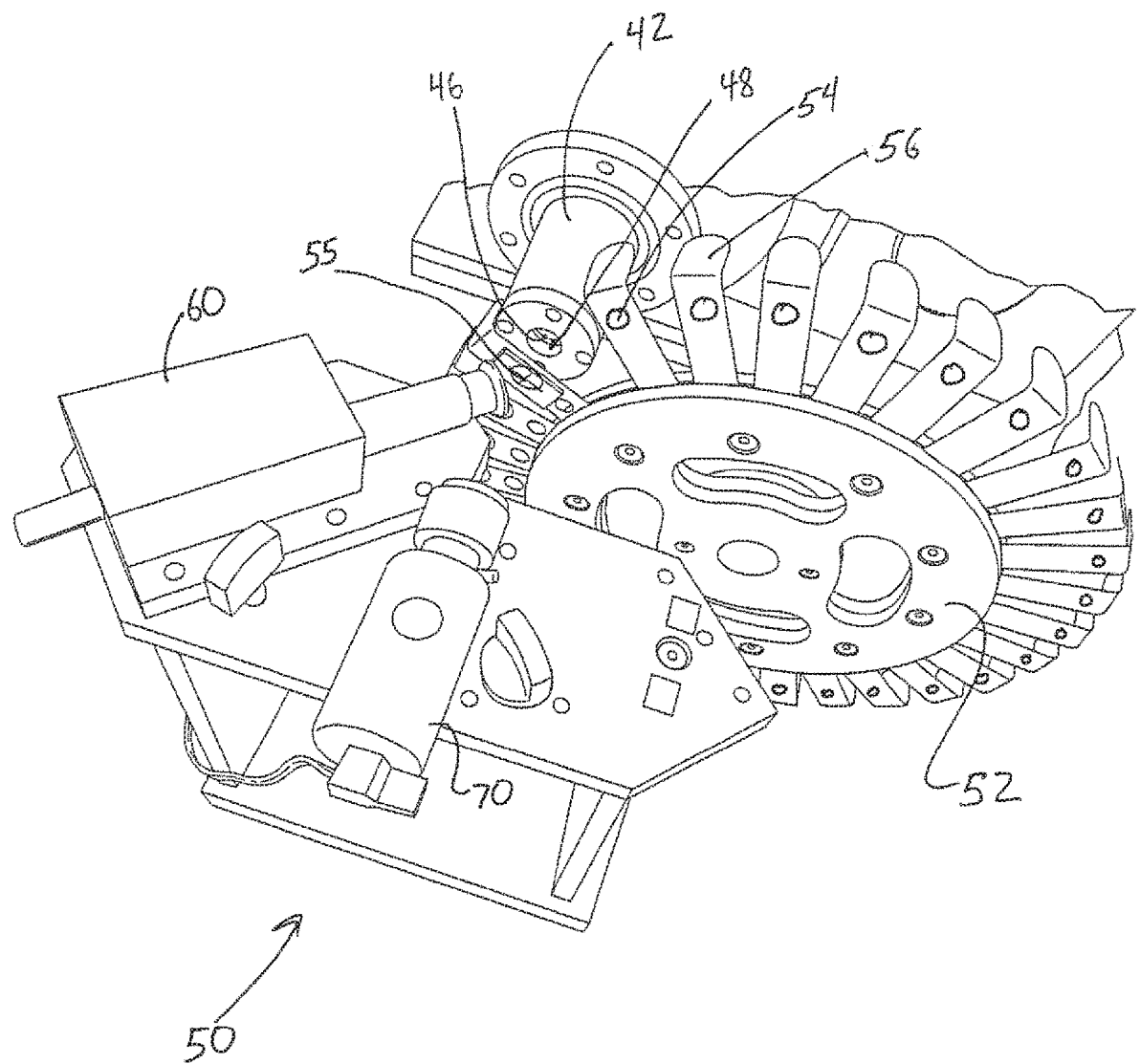
FIG. 4: A perspective view of the target end station, including adjacent beamline structure.

As further illustrated in FIG. 4, the beam 32 of ionized protons 34 is focused and directed through a thin layer of material such as a thin film 46. The thin film 46 separates the high vacuum in the beamline structure 40 from the ambient pressure or low vacuum at the target end station 50. In the illustrated embodiment, the thin film 46 allows the beamline structure 40 to be under high vacuum and the material samples to be at the ambient surrounding pressure. It has been found that a thin layer of a polyimide film provides good results, and generally does not interfere with the measurement of the fluorine peaks as illustrated in FIG. 3. The two peaks, one at 110 KeV and another at 197 KeV are shaded for illustration purposes in FIG. 3. In addition, it has been found that a thin metal film such as Havar® may be used. Any film 46 that allows easy passage of beam of ionized protons with little effect may be used. Whatever film 46 is chosen, it should not interfere with accurately and precisely detecting the absence or presence of the desired element, such as fluorine in the sample of material 8, or measurement of the amount present in the sample of material 8. More specifically, too thick of a film may not allow the charged particles or ionized protons to pass through the film, or at least pass through with sufficient energy and in sufficient quantity to be used to create measurable gamma rays from the target element. In addition, a film that includes the same element as the target element is generally not desirable, as gamma ray emissions from the interaction of the charged particles with the film 46 may give false readings and/or inaccurate measurements, although careful placement of the gamma ray detector may reduce or eliminate such false readings. As such, if the target element is fluorine, as in primary embodiment of the present invention, it is believed that the thin film 46 should be free of fluorine or substantially free of fluorine, and also, minimize any elements or compounds that provide gamma ray peaks at on overlapping position with fluorine. As illustrated in FIG. 3, various peaks are present for different elements, and if gamma rays are given off that slightly overlap the area for the target element, it could give a false positive, and also an inaccurate analysis of the amount present in the sample material. Substantially, free means that when the beam of ionized protons pass through the thin film, the resulting gamma rays do not interfere with the measurement of the target element by adding measurable amounts, such as to the illustrated gamma ray peak for fluorine in FIG. 3. Of course, the thin film 46 must be strong enough to withstand the pressure differential created by the vacuum in the beamline structure 40 versus the atmospheric pressure outside of the beamline structure 40. In the illustrated example, a thin Kapton® film separates the vacuum system in the beamline structure 40 from atmosphere. The Kapton® film used in this example is SPEX SamplePrep 3511 Kapton with a thickness of ⅓ of a mil (0.0085 mm). This film is indicated schematically in FIG. 1, and immediately outside the vacuum foil window a gamma-ray detector 60 is located at an angle of approximately 45° with respect to the beam axis. The gamma rays are emitted in all directions, and the angle of detection is not critical to this measurement. Measurements are routinely made at both 45° and 135° with respect to the beam axis. Therefore, as illustrated in FIG. 4, the detector 60 is set about 45 degrees to the beamline, facing the direction of origin of the beam, as the gamma ray emitted travels forward in the same direction as the beam of ionized protons and outwardly therefrom.

The target end station 50 is configured so that distance between the center of the target and the exit of the vacuum system, i.e. the film 46, is minimized (about 1 cm in this example). As discussed above, the beam of ionized protons loses energy under atmospheric conditions, which is why particle accelerator literature teaches away from analysis of samples in atmospheric conditions. Any gamma-ray detector can be used to detect the resultant gamma rays from the proton irradiation, but a solid-state detector results in the lower noise and higher resolution signals, shown in FIG. 3. The specific detector used in this example is an AMPTEK XR-100T Cd/Te detector, attached to an AMPTEK PX5 Digital Pulse Processor to convert the detector signals into digital spectra, as illustrated in FIG. 4. A twenty percent high-purity Germanium detector has also been used to measure these gamma rays with its own amplifier and analog-to-digital signal processing.

Figure 6:
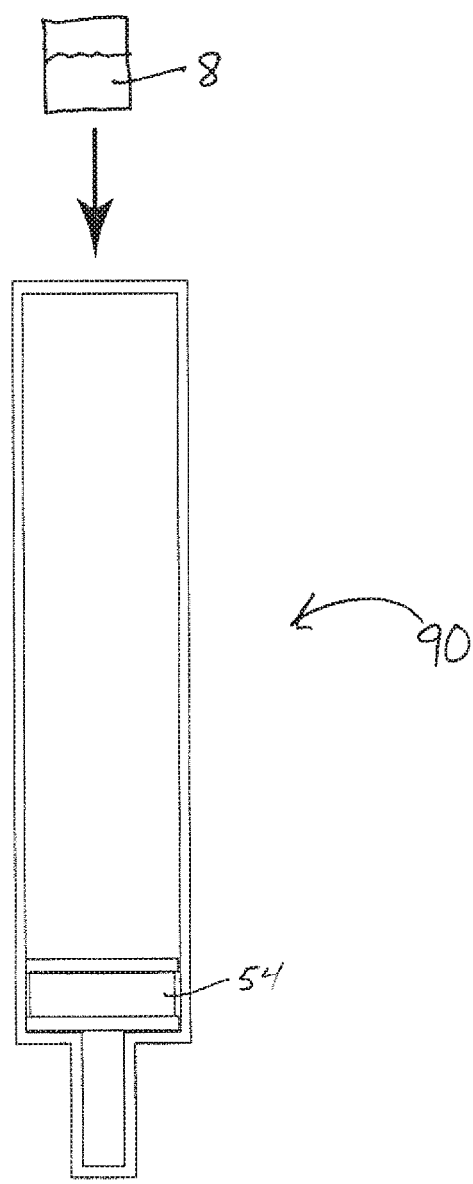
FIG. 6: A schematic diagram of a solid-phase extraction column used to concentrate the target analyte, such as, PFASs from aqueous samples onto a solid matrix material held between two frits.
Figure 7:
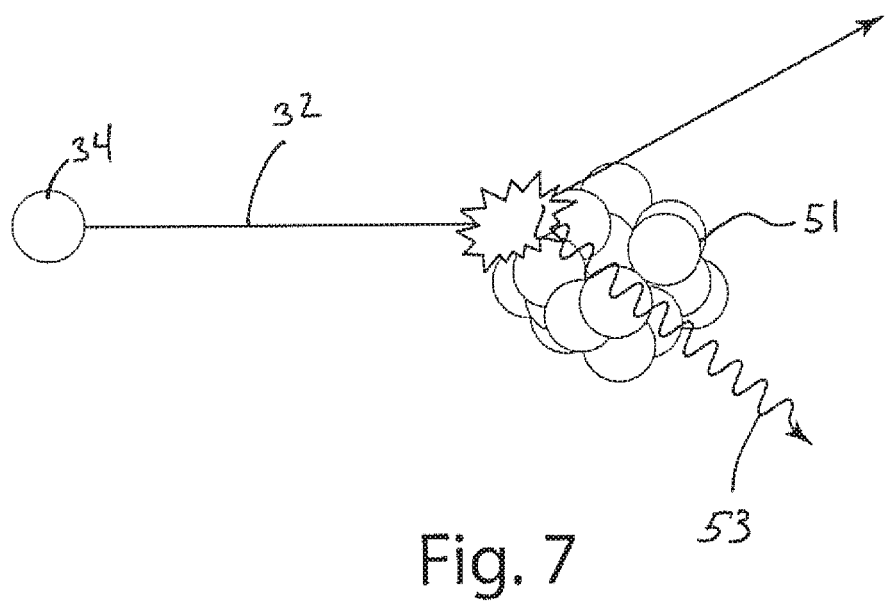
FIG. 7: An exemplary diagram of a proton striking a fluorine nucleus and a gamma ray being created.
Figure 8:
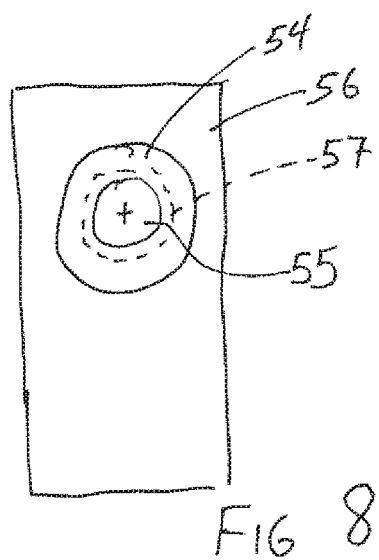
FIG. 8: An exemplary target frame and target.

For aqueous samples, the PFASs are first be extracted by standard solid-phase extraction methods onto a matrix material contained typically in a column, such as shown in FIG. 6. In most samples of material, the PFASs are present in an amount below the detection limit of PIGE, and therefore, solid-phase extraction concentrates the desired target analyte, fluorine in the preferred embodiment, from the sample of material 8. Solid-phase extraction and concentrate the PSASs over a hundred times in order to detect it.

Solid phase extraction is a sample preparation process by which compounds that are dissolved or suspended in a liquid mixture are separated from other compounds in the mixture according to their physical and chemical properties. Solid phase extraction may be used to concentrate and purify samples for analysis as wide ranging as blood, tissue, soil, ground water and more. Solid phase extraction uses the affinity of solutes dissolved or suspended in a liquid (known as the mobile phase) for a solid through which the sample is passed (known as the stationary phase) to separate a mixture into desired and undesired components. The solid phase extraction may be performed such that either the desired analytes of interest are retained on the stationary phase or the undesired impurities are retained on a stationary phase leaving the analytes of interest in the mobile phase. In the present invention, the solid phase extraction is used typically used to capture the PFASs on the stationary phase as described below. The sample of material 8 captured on the solid phase or disk forming the target 54, is hereinafter referred to as the extracted analyte. The extracted analyte will include the target analyte, which is the focus of the analysis, such as PFASs in the preferred embodiment. It should be noted that as the present invention is capable of directly analyzing aqueous samples, due to its unique in atmosphere location of the targets, but the solid phase extraction may be used to concentrate the PSASs from the mobile phase, which makes it more a more sensitive measurement in solid targets 54.

Typical solid-phase extraction media for a broad range of PFASs include the Weak Anion Exchange columns made by Agilent, which comprise a plastic tube with two porous plastic frits that hold a quantity of coated silica beads in place. The silica beads are coated with a neutral primary amine modified divinyl benzene polymer to capture the PFASs in solution as they pass through the column. For PIGE analysis, the Weak Anion Exchange columns are prepared in advance by eluting 4 mL of 0.1% ammonium hydroxide in Optima-grade LC-MS methanol, then 4 mL of Optima-grade LC-MS methanol, and then 4 mL of distilled water. Then, the sample is loaded into the prepared column and after the aqueous solution is passed through the solid-phase extraction column, the column is air-dried for at least 30 seconds, but as long as 2 minutes, and then approximately 150 microliters of cyanoacrylate adhesive is passed through the column by vacuum filtration. The cartridge forming the target 44 should be dry enough to add the cyanoacrylate adhesive, as water causes the cyanoacrylate to set. The cyanoacrylate adhesive (or another adhesive) adheres the WAX cartridge into a solid target, which is suitable for use in the accelerator. Without the adhesive or a different cartridge, the loose beads, including the surface beads where the fluorine is located could move or be lost and provide inaccurate readings. The cartridge is allowed to air dry for at least 3 hours typically, but up to a maximum of 24 hours. For all aqueous samples, the passage of water and cyanoacrylate glue occurs through assistance, such as vacuum filtering. While the above times are for vacuum filtered and dried, it could also be gravity filtered and optionally be air dried without assistance, which would take longer. The air drying of the column currently occurs by allowing air to pass through as part of the vacuum process, such as by a diaphragm vacuum pump. At this time the plastic column and two frits are cut away from the solid disk of silica beads, cyanoacrylate adhesive and PFASs. These disks are the targets 54 with the front surface of these disks including the extracted analyte, becomes the target area for subsequent PIGE analysis. While any solid-phase extraction material may be used, the Weak Anion Exchange cartridges described here are typically used for most fluorinated chemicals, but others may be used to extract fluorinated chemicals as well. If the total amount of fluorine in the sample of material 8 is desired, these disks forming the target may be analyzed using nondestructive PIGE and then later using more conventional techniques, if desired.

If it is desirable to distinguish the fluorine signal arising from PFAS from the fluorine signal arising from inorganic fluoride ions, which are only weakly bound to the WAX cartridge, after the solid phase extraction step, the solid phase in the Weak Anion Exchange cartridges can be rinsed with 4 mL of 25 mL ammonium acetate buffer (of pH 4) before the addition of cyanoacrylate adhesives. This rinse will remove 99% of the fluoride ions preferentially, without removing PFASs. The target 54 including the extracted analyte of the sample of material 8 may then be analyzed using the particle accelerator.

For example, the present invention may take samples of groundwater, extract the PFASs by solid-phase extraction onto a solid material target 54, mount this target 54 to a target frame 56, which is placed in the target end station 50 with the target 54 in front of an accelerated particle beam in air, and the resultant gamma rays from target analyte in the extracted analyte, such as an irradiated fluorine nuclei 51 are detected in an adjacent solid-state gamma-ray detector. Software analysis will yield the number of gamma-rays 53 attributed to fluorine per unit of beam incident on the target. After PIGE analysis is complete, the target 54 including the extracted analyte may be immersed in a solvent to remove the target analyte, such as the PFASs and may be measured by traditional methods as well. Use of PIGE to determine the presence or absence of fluorine eliminates the possibility of false positive or false negative that exists with traditional methods, and easily allows hundreds of samples, if not more, to be processed for the presence or absence of fluorine in a single day. In addition, since PIGE is nondestructive, the sample may be double checked regarding the quantity of target analyte present.

The individual targets 54 to be analyzed are may be adhered to a metal frame or target frame 56 with two sided tape, modeling clay or any other type of adhesive material, preferably fluorine free and the metal frame has an opening 57 through which non-interacting beam particles may pass without interacting with the metal frame 56. While the present invention uses a metal frame to form the target frame 56, supporting the target 54, other materials, sizes, shapes and configurations may be used, and the illustrated target frame 56 is only exemplary.

It is important to focus the beam on the target 54 and away from the of the metal frame 56 to avoid creating gamma rays due to beam undesired beam interactions with the frames which would add to the background noise and which may interfere with accurate measurement of the fluorine peak related to the desired PSASs. Of course, since PIGE does not measure most metals this is not as much of an issue as in PIXE, although if the frames are made from an aluminum material, it could create issues. In exemplary configuration illustrated in FIG. 4, targets 54 may be rotated into the beam of protons 34 remotely by means of an interchangeable target wheel 52 loaded in advance with targets 54 mounted on target frames 56. Of course, the target wheel 52, target supports and targets 54 may be made out of other metals or other nonmetallic materials, all preferably having gamma ray peaks spaced from the peak for fluorine.

In the present invention, at least 1-2 micro Coulombs, preferably 3 to 7 micro Coulombs but typically less than 10 micro Coulombs of beam are delivered to each target and the gamma-ray spectrum is recorded during the bombardment. A spectrum collected with beam on no target for the same length of time can be collected and then subtracted to remove background spectrum. Peaks centered around 110 keV and 197 keV and approximately 20 keV wide are integrated as gamma rays emitted with these energies correspond to two of the eight well-known gamma-ray emissions from fluorine-19. The number of counts in these peaks per micro Coulomb of beam delivered gives a measure of total fluorine-19 content within the irradiation area. Since fluorine is mono-isotopic, and the irradiation area is constant, the number of integrated counts per micro Coulomb of beam represents a direct quantitative measure of total fluorine on the surface of the sample. The technique is non-destructive and reproducible, and may be quantified to absolute concentration with external standards of fluorine.

After PIGE analysis is complete, the target analyte, such as the PFASs trapped in the target 54, such as a disk of silica beds and cyanoacrylate adhesive, may be quantitative removed by dissolving the disk into a solution of acetone or methyl ethyl ketone, or methylene chloride. The target analyte, such as PFASs may be subsequently measured by traditional wet chemistry separations and chromatographic and high-resolution mass spectroscopic methods at this point.

A summary of an exemplary method example from obtaining the sample, to analyzing the results follows.

First, the samples of material 8 must be obtained. Typically all aqueous samples are collected in HDPE containers. These may be are sealed and stored refrigerated until analysis. Other collection methods may be used, and may depend on the type or form of the sample, as well as the desired target analyte. The following method is an example specific to PFASs as the target analyte.

Before analysis, each aqueous sample is thoroughly remixed by >1 minute of manual agitation. Remixing ensures that the target analyte is well distributed through the sample of material 8.

If the sample of material 8 is visibly turbid, it may be centrifuged for a specified time. It has been found that centrifuging for more than ten minutes at an RCF (relative centrifugal force) of more than 1500×g to remove suspended solids works well. As the PFASs are in the aqueous material and not the solids centrifuged out of the sample of material 8, centrifuging works well although it may not be desirable for other target analytes. In addition, any solids remaining could clog or slow down the following solid phase extraction process and therefore, it is desirable to remove the solids. Then the aqueous samples of material 8 are decanted into solid-phase extraction manifold.

The solid phase extraction manifold is prepared by loading conditioned Oasis® WAX (weakly anionic exchange) cartridges for each aqueous sample. The WAX cartridges are previously conditioned by applying 3 mL of 0.1% ammonium hydroxide in methanol, 3 mL of methanol, 3 mL of RO water, and 40 mL of sample, in sequence through the cartridge.

Vacuum filtration may be applied to force the aqueous samples through the solid phase extraction manifold quickly. Typically 40-80 mL of aqueous sample will be pulled through each WAX cartridge to extract all the anionic PFAS chemicals (the target analyte) onto the solid surface of the cartridge as an extracted analyte. The eluent is discarded.

Vacuum may continue to be applied to the WAX cartridges after the aqueous sample has passed through them to dry the cartridge or target 54 for ~30 seconds after the sample has been extracted.

Approximately 150+−5 microliters of cyanoacrylate glue is placed on top of each WAX cartridge forming the target 54 through which aqueous sample has been extracted, and this glue is then pulled through the cartridge/target 54 by vacuum to solidify the modified silica bead of the WAX cartridges into a solid target material 54.

Each WAX cartridge forming the target 54 is allowed to air dry at room temperature for more than 3 hours. Then the solidified disk forming the target, and including the extracted analyte, is extracted manually from the tube of the WAX cartridge and mounted on a target frame 56 for irradiation. This mounting can be done by tape or moldable clay.

A selection of WAX cartridge targets 54 is typically mounted onto a target wheel 52 located at the exit port or terminus of the beamline structure 40 of the ion beam accelerator 10. This exit port has a thin film 46 to maintain vacuum inside the accelerator 10, and yet allow the targets 54 to be analyzed in air.

The ion beam accelerator 10, if not already operating, is turned on to produce a focused beam of high-energy protons (3.4 MeV in this example), and the gamma-ray detector 60 (a high-purity 20% germanium detector in this example) is turned on to capture gamma-ray spectra from each irradiated target 54. The procedures for obtaining a focused ion beam will vary from accelerator to accelerator, but typically this procedure will involve turning on an ion source 20, an accelerating voltage 40, and magnets 44 as beamline steering and focusing elements. Similarly, each gamma-ray detector 60 is unique, but typically high voltage is applied to a high-purity semiconductor crystal, and the resultant energy pulses detected from the passage of ionizing radiation in the detector 60 is passed through electronic amplification, shaping and digitization to be recorded in a data acquisition computer.

The focus and intensity of the beam is measured using scintillators and faraday cups, respectively. Typically, approximately 10 nA of 3.4 MeV protons are focused into a beam with a diameter of approximately 1 mm when impacting the target area 55 on the target 54.

Typically, background spectra (with beam incident on air (with no target), and inorganic fluorine standard spectra (made with NaF homogenized in cellulose nitrate powder by mass) are recorded first and every 4 hours or so during the analysis to confirm ion beam consistency.

For each sample target 54, the beam is measured in a faraday cup before and after data acquisition, to estimate the on-target beam intensity, and typically, gamma-ray spectra are collected for several minutes per target at a beam current of approximately 10 nA.

The resultant spectra from both blanks, standards and samples are stored on networked computer drives. After ion beam analysis is complete on a target, software routines integrate gamma-ray peaks and subtract background radiation are used to count the number of 110 keV and 197 keV gamma rays detected. The gamma-ray detector 60 is independently calibrated periodically (monthly typically) with radioactive sources to determine absolute energy scales.

Analysis of each sample is completed by determining the number of gamma rays measured in both fluorine peaks (110 keV and 197 keV) and dividing by the total charge incident on the target 54. The total beam charge is estimated from the beam intensity (in nA) multiplied by the number of seconds of data acquisition, to give microCoulombs of beam used for analysis. The number of counts/microCoulomb of incident beam is proportional to the total amount of fluorine present on the surface of the target 54. This can be related to the inorganic fluorine standards for an estimate of total target analyte, such as total fluorine extracted from the aqueous sample. By dividing by the total volume extracted, a total fluorine concentration of the original solution and therefore sample of material 8 can be estimated. There are other fluorine gamma rays that can be used to measure fluorine, but these two are the most efficiently detected by these types of detectors.

The invention claimed is:

1. A method of detecting the presence of perfluorinated or polyfluorinated alkyl substances (PFAS(s)) comprising the steps of:

obtaining an aqueous sample of material for analysis;

performing a solid phase extraction on the aqueous sample using a weak anion exchange cartridge to capture any present PFASs in the aqueous sample;

forming a target from the weak anion exchange cartridge;

placing the target in a target end station of a particle accelerator, wherein the target end station and target are ex vacuo and an ion source, accelerator and beamline structure of the particle accelerator are in vacuo;

creating a focused beam of charged particles with the particle accelerator;

directing the focused beam of charged particles to exit the beamline structure through a thin film dividing the ex vacuo target from the in vacuo beamline structure, and wherein the focused beam of charged particles impacts the target to produce gamma rays of different energies;

measuring the wavelength and quantity of gamma rays created by the impact of the focused beam of charged particles against the target; and analyzing the measured gamma rays to determine if peaks in the measured gamma rays are present at 110 keV and 197 keV to determine if fluorine in PSAS(s) is present.

2. The method of claim 1 wherein said step of performing a solid phase extraction further includes the steps of pulling the aqueous sample through the cartridge under vacuum and drying the cartridge under vacuum and wherein said step of forming a target from the weak anion exchange cartridge further includes the steps of passing an adhesive through the cartridge to solidify the cartridge; air drying the cartridge at 16-30 degrees Celsius; and coupling the cartridge to a target frame.

3. The method of claim 2 wherein the target frame defines a hole over which the cartridge is adhered.

4. The method of claim 2 wherein said step of analyzing further includes the step of determining the absence or presence of PSAS(s).

* * * * *